(12) United States Patent
Krell et al.

(10) Patent No.: US 6,479,248 B1
(45) Date of Patent: Nov. 12, 2002

(54) **PROCESS AND AGENT FOR DETECTING ANTIBODIES AGAINST *TREPONEMA PALLIDUM***

(76) Inventors: Siegfried Krell, Immermannstrasse 15, D-39108 Magdeburg (DE); Annegret Gerber, Bruno-Taut-Ring 9, D-39108 Magdeburg (DE)

( * ) Notice: Subject to any disclaimer, the term of this patent is extended or adjusted under 35 U.S.C. 154(b) by 0 days.

(21) Appl. No.: 09/043,959

(22) PCT Filed: Sep. 30, 1996

(86) PCT No.: PCT/EP96/04249

§ 371 (c)(1),
(2), (4) Date: Mar. 30, 1998

(87) PCT Pub. No.: WO97/13151

PCT Pub. Date: Apr. 10, 1997

(30) Foreign Application Priority Data

Sep. 29, 1995 (DE) .......................... 195 36 166

(51) Int. Cl.[7] ...................... G01N 33/53; G01N 33/569; G01N 33/571; C12P 21/04; C12N 1/20
(52) U.S. Cl. .................... 435/7.22; 435/7.32; 435/7.36; 435/7.92; 435/7.1; 435/7.71; 435/71.1; 435/252.3; 435/252.1; 435/260; 435/253.6; 536/23.7
(58) Field of Search .................. 435/7.22, 7.32, 435/7.36, 7.92, 7.1, 7.71, 71.1, 252.3, 252.1, 260, 253.6; 536/23.7

(56) References Cited

U.S. PATENT DOCUMENTS 5,264,360 A 11/1993 Riviere
5,350,842 A 9/1994 Norgard

FOREIGN PATENT DOCUMENTS

| AU | 645970 | 3/1994 |
|---|---|---|
| EP | 0 275 260 B1 | 7/1988 |
| EP | 0 282 042 B1 | 9/1988 |
| EP | 0 391 330 B1 | 10/1990 |
| EP | 0 670 494 A2 | 6/1995 |
| EP | 0 686 696 A1 | 12/1995 |
| WO | WO 88/02403 | 4/1988 |

OTHER PUBLICATIONS

Infection and Immunity, vol. 61, No. 4, 1993, p. 1202–1210, Darrin R. Akins: "Lipid Modification of the 17–Kilodalton Membrane Immunogen of *Treponema Pallidum* Determines Macrophage Activation as Well as Amphiphilicity".
Schouls et al , Overproduction and purification of T.pallidium recombinant –DNA derived proteins TmpA and TmpB and their potential use in serodiagnosis of Syphilis. Infection and Immunity, vol.–57, pp. 2612–2623, 1989.*
Byrne et al , Evaluation of T.pallidium western immunoblot assay as a confirmatorytest for Syphilis. Jur.Clinical. Microbiology, vol.–30, pp. 115–122, 1992.*
Zrein et al , Recombinant antigen–based enzyme immunoassay for screening og T.pallidium antibodies in blood bank routine. Jur.Clinical.Microbiology. vol.–33, pp. 525–527, 1995.*

* cited by examiner

*Primary Examiner*—Lynette R. F. Smith
*Assistant Examiner*—Padma Baskar
(74) *Attorney, Agent, or Firm*—Salter & Michaelson

(57) ABSTRACT

A method and agent for antibodies against *Treponema pallidum* are provided. The method involves gene-amplifying and cloning a selection of recombinant antigens. The selection of recombinant antigens consists of 17 kD antigen, 47 kD antigen and TmpA. The antigens are expressed in host vector systems, followed by purification. The purified antigens are then bound to a solid phase individually or in combination, and subjected to a reaction with a clinical specimen. The antibodies bound from the clinical specimen by means of an antigen/antibody reaction are determined by means of a detection system wherein the selection of the recombinant antigens for detecting antibodies to *Treponema pallidum* consists of 17 kD antigen, 47 kD antigen and TmpA.

18 Claims, 8 Drawing Sheets

Fig.3
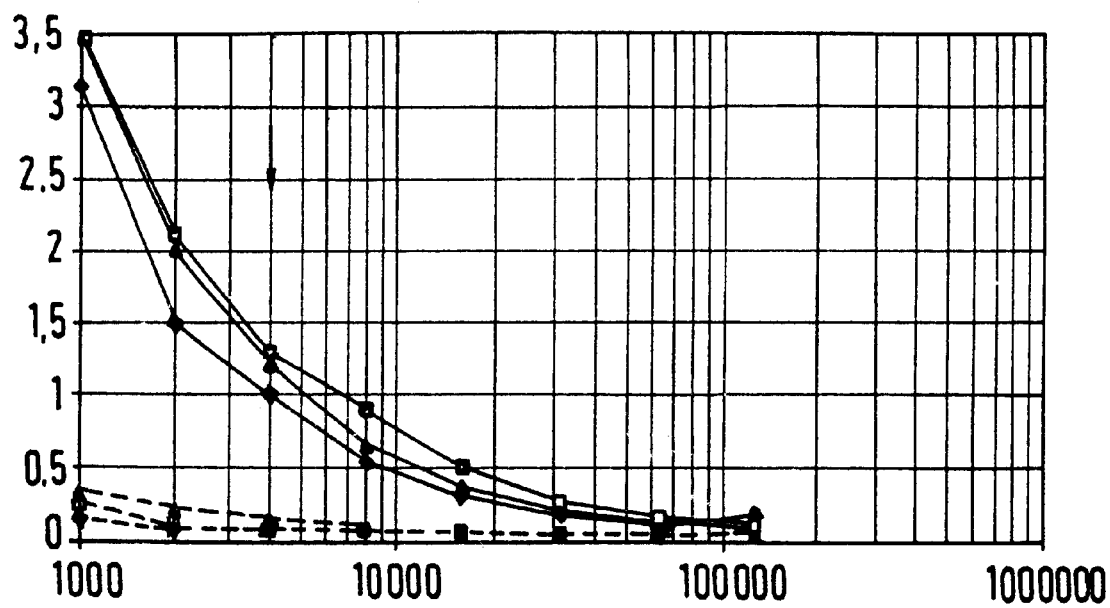
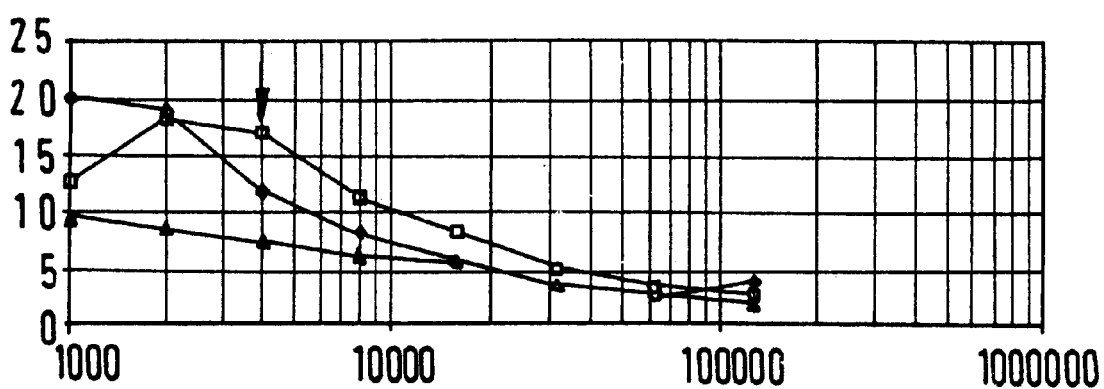

Fig.7
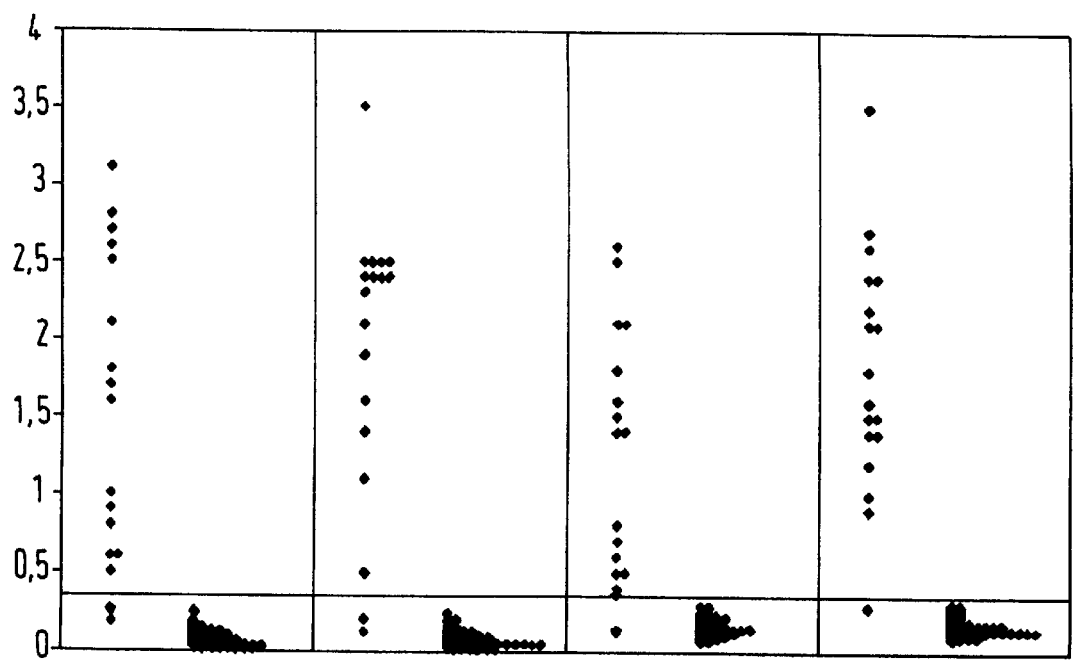
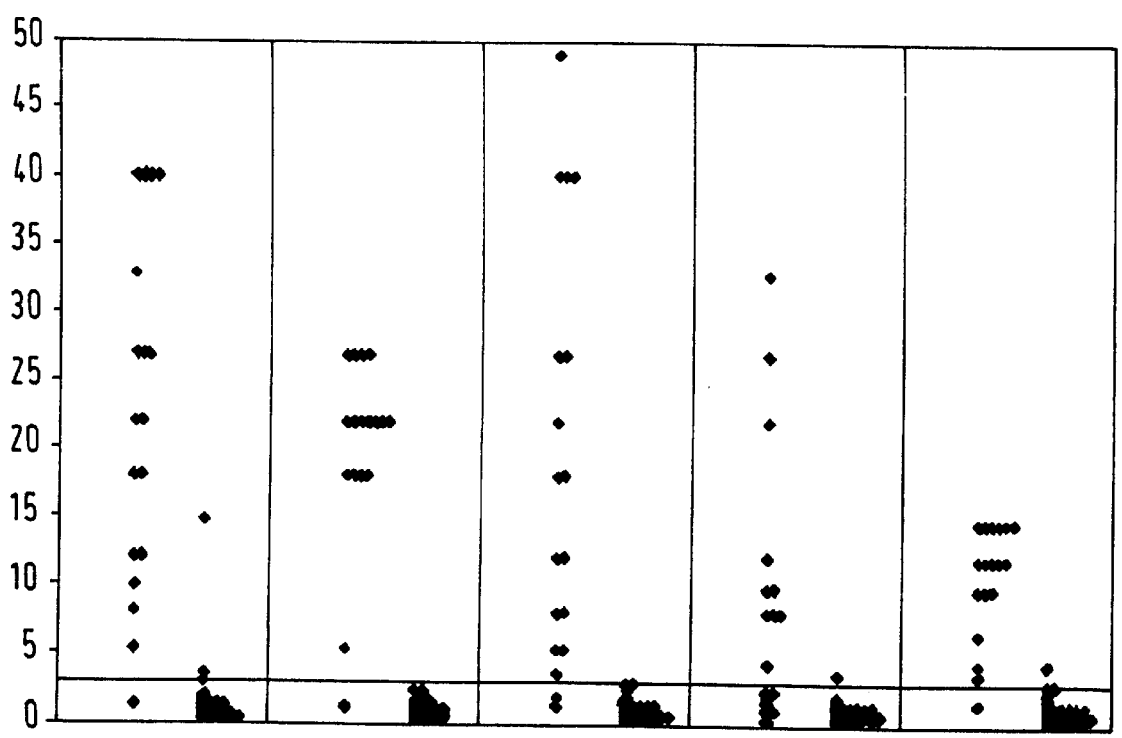

PROCESS AND AGENT FOR DETECTING ANTIBODIES AGAINST *TREPONEMA PALLIDUM*

BACKGROUND OF THE INVENTION

1. Field of the Invention

This invention relates to a method and agent for the detection of antibodies to *Treponema pallidum*.

2. Related Art

*Treponema pallidum* is the causative agent of syphilis. Diagnosis of infections with this pathogen is important not only when infection is suspected, but it is also of great significance to exclude syphilis among pregnant women and blood donors. In prenatal care, the purpose of such diagnosis is to prevent congenital syphilis, i.e. a transfer of syphilis to the neonate, and any consequent harm to the child. Negative serologic results for syphilis constitute one selection criterion for blood donors.

Syphilis is primarily diagnosed serologically, i.e. by the detection of antibodies to *Treponema pallidum* and/or cardiolipin. Specific IgM antibodies are detectable already 14 days after infection and IgG antibodies at the latest from 4 weeks after infection. Only before that time is direct detection of the causal agent from infected tissue of the primary lesion is another decisive diagnostic criterion.

Diagnosis by culture, as is conventional for many other bacterial pathogens, is not possible as *Treponema pallidum* has not hitherto successfully been cultured in vitro, with the exception of propagation in cell cultures (U.S. Pat. No. 5,264,360).

Serologic detection methods may be divided into three groups depending upon the nature of antibody detected:

1. Nontreponemal tests. Tests such as the cardiolipin microflocculation test (CMT), which is known in the English-speaking world as the Venereal Disease Research Laboratory Test (VDRL test), the rapid plasma reagin test (RPR test) and the cardiolipin complement binding reaction (cardiolipin CBR) are based on the detection of antibodies to cardiolipin. These tests reveal positive results 3–5 weeks after infection or approx. 7–10 days after appearance of the primary lesion. Sensitivity is 60 to 87% in the primary stage and may be as high as 100% in secondary syphilis. Sensitivity does, however, fall in the later stages of the disease, such that up to 30% of the late stages are no longer reactive. When the VDRL test is performed quantitatively, titre may be correlated to the activity of the disease. The disadvantage of this test is the large proportion of 0.3–0.9% of false positive test results when screening blood donors and the occurrence of false negative results in sera having an elevated titre due to the prozone phenomenon, which may be observed in 1–2% of cases in the VDRL test in secondary syphilis.

2. Treponema-specific tests. Antibodies to the endoflagellae of *Treponema pallidum* are formed as syphilis progresses. As a result of antigen relatedness, these antibodies also react with the endoflagellae of other species of treponema. The endoflagellae of *Treponema phagedenis* (biotype Reiter) have thus also been used as an antigen for the diagnosis of syphilis (Flagellum ELISA, R. V. W. van Eijk et al., *Genitourin. Med.* 62, 367–372 (1988)). In the flagellum ELISA, the cut off for a positive test result is a compromise between sensitivity and specificity, as a result of which 0.8% of results are false positives and 2.7% false negatives.

3. *Treponema pallidum*-specific tests. These tests detect antibodies which react with *Treponema pallidum* or antigen preparations from this pathogen. These test systems include the *Treponema pallidum* haemagglutination test (TPHA), the fluorescent *Treponema pallidum* antibody absorption test (FTA-ABS) and the Nelson test (*Treponema pallidum* immobilisation test, TPI) together with ELISA systems based on sonicate antigen. TPHA and FTA-ABS are generally used in diagnostics.

The Nelson test involves a microscopic assessment of the extent to which complement activating antibodies in the patient's serum inhibit the mobility of *Treponema pallidum*. Due to its high cost, the Nelson test is used virtually exclusively for scientific investigations.

In TPHA, erythrocytes to which the *Treponema pallidum* sonicate antigen is bound are agglutinated by serum antibodies from syphilis patients. At a false positive rate of 0.07% and false negative rate of 0.008%, TPHA is highly specific and sensitive with most false negative results occurring in the initial stage of syphilis. TPHA is positive starting from the $4^{th}$ week of infection, exhibits sensitivity of 64% to 87% in primary syphilis with an initially low titre (80–320) which, on transition to secondary syphilis, may rise to above 5000 at a sensitivity of 100%. As the disease progresses further, TPHA remains positive when the titre has a tendency to fall during the latent stage.

In FTA-ABS, indirect immunofluorescence microscopy is used to detect the binding of specific antibodies in the serum under investigation onto *Treponema pallidum* attached to a solid support via a fluorescent-labelled secondary antibody. Sensitivity of detection is 86% to 100% in primary syphilis, reaches 100% in secondary syphilis and 96% to 100% in the late stages. According to various sources, sensitivity for all stages is between 83% and 95%. Specificity, at 83% to 89% (excluding "borderline" findings) is not very high. Isolated FTA-positive sera with an otherwise negative syphilis serology are caused, for example, by Lyme borreliosis. FTA-ABS is performed as a confirmatory test to validate positive TPHA findings. Veldkamp and Visser (*Brit. J. Vener. Dis.* 51, 227–231 (1975)) provide the first description of an ELISA (enzyme-linked immunosorbent assay) in which the sonicate antigen of *Treponema pallidum*, which is adsorptively bound to solid phases, reacts with specific antibodies from the material under investigation. The bound antibodies are detected by reaction with an enzyme-labelled, species-specific secondary antibody to class IgG or IgM immunoglobulins and a subsequent enzymatic colour reaction. The commercial indirect enzyme immunoassay Captia Syphilis G (Mercia Diagnostics, Guildford, England) is also based on this principle. This assay has been found to have a sensitivity of 98.4% and a specificity of 99.3% (Young et al., *J. Clin. Pathol.* 45, 37–41, (1992), *Genitourin. Med.* 65, 72–78 (1989)). Captia Syphilis M detects a specific IgM which is formed right at the early stages of the disease (sensitivity in primary syphilis 82%). Since IgM antibodies cannot pass through the placenta, this assay is of significance in the diagnosis of congenital syphilis (sensitivity 100%, Ijsselmuiden et al., *J. Clin. Microbiol.* 27, 152–157, (1989)). The assay is based on the principle of a solid phase bound capture antibody for IgM from the material under investigation, wherein specific IgM antibodies subsequently react with *Treponema pallidum* antigen. Detection is by means of an enzyme-labelled monoclonal antibody to endoflagellae and subsequent enzymatic colour reaction.

In the Syphilis BioEnza Bead Assay (Organon Teknika Corp., USA), the *Treponema pallidum* antigen is adsorptively bound to ferromagnetic particles. Binding of antibodies from the material under investigation is then detected by means of enzyme-labelled secondary antibodies and colour reaction. The sensitivity and specificity of this test are stated at 93% and 98.6% (Burdash et al., *J. Clin. Microbiol.* 25, 808–811, (1987)).

The sonicate antigen mentioned above is obtained by mechanical processing of the pathogen with ultrasound.

The deficient in vitro culturability of *Treponema pallidum*, which has already been mentioned, naturally means that these pathogens can be made available only with great difficulty.

Two-stage diagnosis of syphilis is currently generally recognised. In the first stage, all the sera are investigated with a test (screening). In the second stage, positive sera are investigated with another test system (confirmatory test). Since, in many countries, the incidence of syphilis is low (<1%), 99% specificity of the screening test is not sufficient to ensure reliability of diagnosis. A positive predictive value of above 90% is only achieved with a confirmatory test based on a different detection principle.

Screening is widely performed using TPHA alone or in combination with the VDRL test or RPR test and the resultant positive sera are verified by FTA-ABS as the confirmatory test.

Performing the VDRL test or RPR test quantitatively is a recognised method for monitoring treatment, wherein a more than four-fold fall in titre is considered to indicate success of the treatment.

Valuation of current syphilis diagnostics: non-treponema-specific tests yield approx. 5% false positive results. They are thus suitable only as a first stage for serological diagnostics and, in the event of a positive result, must be complemented in the second stage by *Treponema pallidum*-specific tests. Since quantitative evaluation of non-treponema-specific tests may be correlated with the activity of the disease, such tests may be used to monitor the success of antibiotic treatment.

False positive test results in the treponema-specific tests are possible due to the relatedness of the antigens to treponema which occur in humans as commensal organisms in the oral mucosa. These test systems cannot gain general acceptance for diagnosing syphilis due to their deficient specificity and sensitivity.

*Treponema pallidum*-specific tests are based on *Treponema pallidum* antigen preparations, wherein, due to the deficient in vitro culturability of *Treponema pallidum*, the bacterial antigen used is obtained from infected rabbit testes. This method is associated with animal welfare considerations and only small quantities of antigen may be produced. The FTA-ABS and Nelson test are costly to perform and are not suitable for automation. Since antibodies to non-pathogenic treponema may also occur in healthy subjects and, due to relatedness of the antibodies, they exhibit cross-reactivity with *Treponema pallidum* sonicate antigen, the use of *Treponema pallidum* whole antigen requires serum absorption with Treponema phagedenis preparations.

While ELISA systems based on *Treponema pallidum* as a whole antigen do indeed satisfy quality criteria with regard to sensitivity and specificity, due to high cost, however, they are not suitable to replace the widely used two-stage diagnostics with TPHA, VDRL test or RPR test in combination with FTA-ABS.

It has already been established in EP 0 391 330 B1 that commercially available tests also do not fulfil the requirements placed on screening tests with regard to reasonable technical complexity and test evaluation. It is proposed in this document to remedy these defects by binding the antigens to a solid phase, either irreversibly directly or via a non-immunochemically binding spacer.

The object of the invention is accordingly to provide a method and agent for detecting antibodies to *Treponema pallidum* which allow this situation to be improved.

SUMMARY

This object is achieved by a method in which a selection of recombinant antigens is gene-amplified and cloned, these gene-amplified and cloned antigens are subsequently expressed in host vector systems and then purified and the purified antigens are then bound to a solid phase individually or in combination, the antigens bound to the solid phase are then subjected to a reaction with a material to be investigated for antibodies, and determination of antibodies bound via antigen/antibody reaction qualitatively and/or quantitatively by means of a detection system.

Such a method for the first time provides a method which is reasonable with regard to technical complexity and simultaneously achieves the necessary maximum sensitivity and specificity when determining antibodies to *Treponema pallidum*.

A means according to the invention of the method for detecting antibodies to *Treponema pallidum* consists of the recombinant antigens 17 kD antigen, 47 kD antigen and TmpA.

A combination of these three antigens results in an elevated diagnostic sensitivity in serological syphilis diagnostics. It allows the simultaneous detection of antibodies to antigens to which elevated antibody concentrations are to be found in all stages of syphilis.

In certain applications, it is preferred to add certain recombinant antigens either individually to the above-stated three or also in groups of two or more to the above-stated three. These added antigens are BMP, the 34 kD antigen, TmpC and Tp4.

Addition of these recombinant antigens is preferred in certain applications because additional detection of antibodies against *Treponema pallidum*-specific epitopes of these recombinant antigens may bring about a further improvement in sensitivity of the serological detection of syphilis.

The following preconditions apply to the optional addition of these recombinant antigens in order to avoid reductions in specificity:

1. non-specific binding must be minimised.
2. cross-reacting antibodies in the material under investigation must be removed or neutralised, for example by absorption.

When making combined use of recombinant antigens, it must be ensured for the particular embodiment that antibodies to each individual antigen generate a substantial proportion of the detected signal (increase in absorbance, chemiluminescence, radioactivity, fluorescence etc.).

While proposals have indeed already been made to clone *Treponema pallidum* DNA to overcome deficient in vitro culturability, no commercially usable diagnostic systems have come into being which are able to match the sensitivity and specificity of prior art syphilis diagnostics. Accordingly, only speculation is known from the literature, but no reports of serodiagnostic methods for syphilis using a combination of recombinant antigens.

It has been found that one fundamental problem associated with serum diagnostics using single antigens is that the level of antibodies for the individual antigens depend not only upon the stage of the disease, but also on idiosyncratic, individual differences. Combined antibody detection of two diagnostically relevant antigens, i.e. a selection thereof, may accordingly increase the sensitivity and specificity of the serological diagnostics.

Further, preferred means according to the invention are stated in the subordinate claims.

Another decisive factor for test systems using recombinant proteins is the purity thereof. When using recombinant antigens from expression systems with E. coli, it is necessary to remove the host proteins as completely as possible as natural antibodies to this intestinal bacterium are otherwise detected in the test system. The production of recombinant proteins using a cloning strategy, expression and purification of the recombinant proteins used, is thus of considerable significance to the particular test method.

The method according to the invention is based on the reaction of specific antibodies, in particular from body fluids such as serum, plasma or spinal fluid, with recombinant antigens of Treponema pallidum, which are bound to a solid phase. Antibodies bound by a specific antigen/antibody reaction are preferably detected by a secondary, labelled antibody. Labelling may be achieved by radioactive labels, fluorescent dyes or enzymes. The parameter measured is the bound radioactivity (principle of the radioimmunoassay), fluorescence (fluorescent immunoassay), enzyme activity by a substrate colour reaction (calorimetric immunoassay) or a substrate reaction with chemiluminescence (chemiluminescent immunoassay). In order to illustrate the described essentials of the invention by way of example, methods using colormetric and chemiluminescent detection are presented.

The antigens are bound to a solid phase using various principles. Possible binding principles are adsorptive binding, covalent binding or binding by reaction with a specific capture antibody already bound to a solid phase. Support materials which may be used are microparticles, beads, rods, tubes and microtest plates or porous materials. Test systems using microtest plates, to which the antigens have been adsorptively bound, and a detection method with the antigens covalently bound to paramagnetic particles are presented by way of example.

This method is used together with a selection of Treponema pallidum recombinant antigens. The genes for the 17 kD antigen, for the 47 kD antigen, TmpA, TmpC and BMP, the 34 kD antigen and Tp4 were amplified from Treponema pallidum DNA by polymerase chain reaction, inserted into the plasmid vector pQE-30 and transformed in E. coli M15[pREP4]. The host/vector system used allowed inducible expression of the recombinant proteins with subsequent purification of the recombinant proteins by affinity chromatography, the proteins then being bound to the solid phase.

The present invention furthermore provides the method for the selection of the recombinant antigens which are suitable for syphilis serodiagnostics by testing the antibody content of patient sera from different stages and the combined detection of antibodies to selected Treponema pallidum antigens.

BRIEF DESCRIPTION OF THE DRAWINGS

Preferred embodiments of the invention are described below with reference to the attached Figures, which show:

FIG. 3 a calorimetric ELISA to show the dependency of absorbance and positive/negative quotient on conjugate dilution;

FIG. 7 a colorimetric ELISA and a chemiluminescent ELISA to detect antibodies to Treponema pallidum in patient sera;

DESCRIPTION OF THE PREFERRED EMBODIMENTS

The cloning, expression and purification of the Treponema pallidum antigens are explained below by way of example using the Figures.

Polymerase chain reaction (PCR) gene amplification for selected Treponema pallidum antigens was performed on Treponema pallidum DNA using specific cloning primers. The resultant PCR product was cut by the restriction endonucleases BamHI and SalI and then inserted by ligation into the expression plasmid vector pQE-30 cut by BamHI/SalI. E. coli M15[pREP4] is then transformed. The plasmid vector and host are described in The QIA-expressionist, published by Qiagen Inc., Chatsworth, Calif. 91311, US, from whom the vector and host are also available, and reference is furthermore made to EP 0 282 042 B1.

Expression of the recombinant antigens may purposely be induced in the clones obtained in this manner. Purification by affinity chromatography is made possible by the expression system used and yields recombinant antigens of sufficient purity for diagnostic tests.

Pre-selection of strong Treponema pallidum immunogens then follows. Over the course of syphilis, antibodies to numerous Treponema pallidum proteins are formed (Norris, Microbiol. Rev. 57, 750–775 (1993)). A western immunoblot is performed to identify strong immunogens. To this end, Treponema pallidum whole antigen is separated by sodium dodecyl sulphate polyacrylamide gel electrophoresis (SDS-PAGE) and the proteins transferred onto nitrocellulose (western blot).

Figure 1:
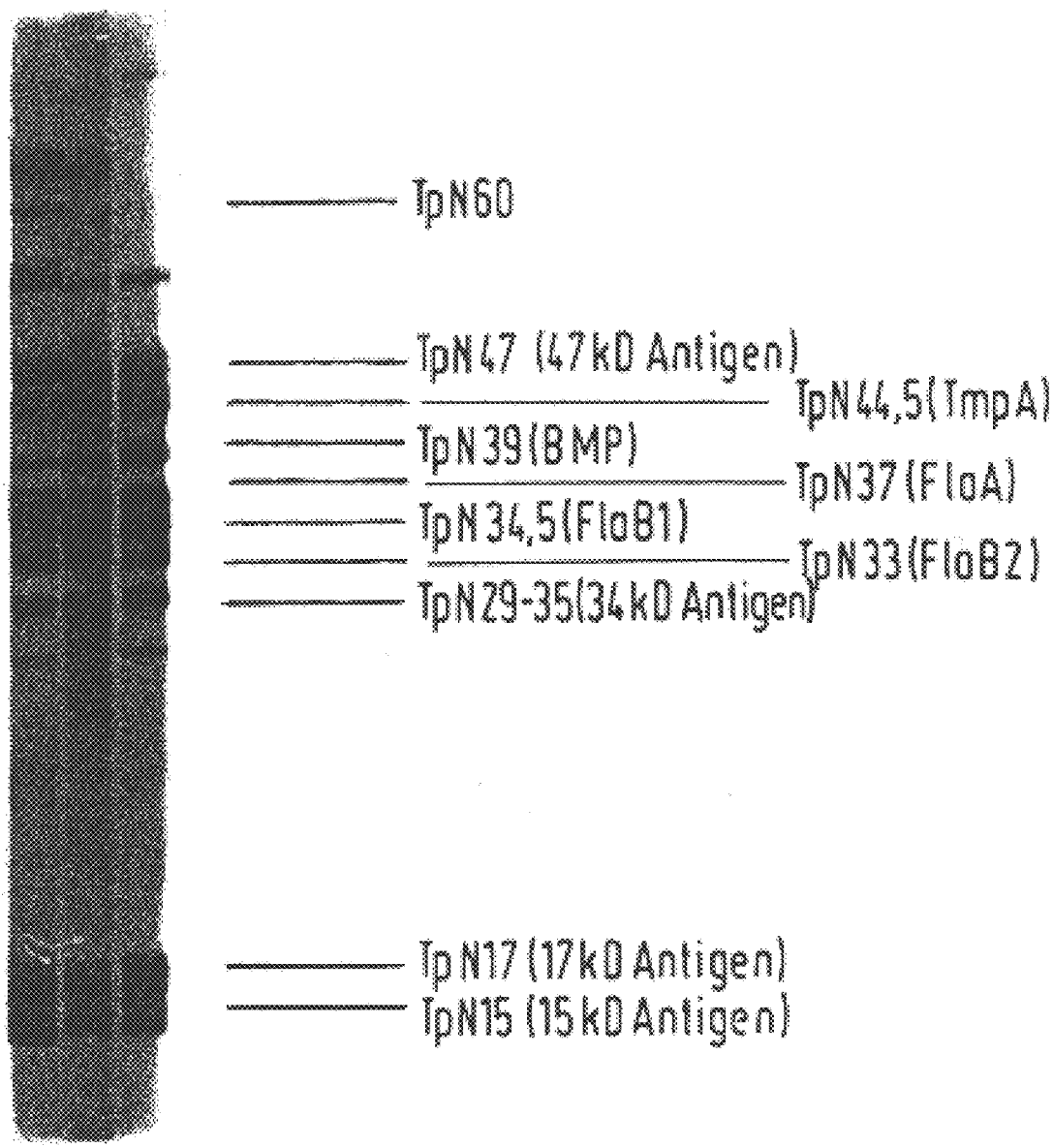
FIG. 1 a western immunoblot with the antigen profile of Treponema pallidum.

FIG. 1 shows the result. After incubation with a pooled serum from patients with secondary syphilis (track 1), with a primary syphilis patient serum (track 2) and a secondary syphilis patent serum (track 3) followed by incubation with a horseradish peroxidase-conjugated anti-human globulin, immunoreactive antigens were revealed by the ECL™ detection system (Amersham). From the top downwards, the arrows indicate TpN60, TpN47 (47 kD antigen), TpN44.5 (TmpA), TpN39 (BMP), TpN37 (FlaA), TpN34.5 (FlaB1), TpN33 (FlaB2), TpN29–35 (34 kD antigen), TpN17 (17 kD antigen) and TpN15 (15 kD antigen). The designations stated before the brackets are those corresponding to the nomenclature recently introduced by Norris (c.f. above), those stated between the brackets correspond to the generally used nomenclature.

Patient sera with separated Treponema pallidum whole antigen here exhibited strong reactivity in bands corresponding to the 15 kD antigen, the 17 kD antigen, the 34 kD antigen, the endoflagellum antigens (FlaB1, FlaB2, FlaA), BMP, TmpA and the 47 kD antigen.

Due to the known antigen relatedness with homologous proteins from other treponema species, the endoflagellum antigens are not selected. The other antigens are cloned and, with the exception of the 15 kD antigen, expressed.

The *Treponema pallidum* antigens are cloned as follows: *Treponema pallidum* is obtained from infected rabbit testes and the genomic DNA is beeing isolated by a modified proteinase K/SDS method. The polymerase chain reaction (PCR) gene amplification proceeds with the assistance of specific primers (Table 1) such that restriction endonuclease restriction sites (BamHI on the 5' end, SalI on the 3' end) allow the incorporation of the PCR amplification products into the corresponding cloning site of the pQE-30 vector.

Table 1 at the end of the description shows the cloning primers for gene amplification of the *Treponema pallidum* antigens. In the table, the restriction endonuclease restriction site is shown in bold, the first amino acid coded by the PCR amplification product is in italics (TGT and TGC are cysteine, CAG is alanine and AAG is lysine); the stop codon is underlined.

PCR is performed in a final volume of 100 μl and contains 50 mM KCl, 10 mM tris HCl pH 8.3, 1.5 mM $MgCl_2$, deoxyribonucleotide mix (200 μM each of ATP, GTP, TTP, CTP), 100 pmol each of cloning primers 1 and 2 (Table 1), 1 ng of chromosomal *Treponema pallidum* DNA or 20 ng of plasmid DNA with an inserted *Treponema pallidum* gene sequence and 1 unit of Taq polymerase (Pharmacia). The reaction mixture is covered with a layer of 100 μl of oil (mineral oil, SIGMA). The reactions are performed in a thermocycler (Landgraf) (denaturation 60 s, 94° C., annealing 120 s, 50° C., polymerisation 120 s, 72° C.). The size of the PCR products is verified by means of agarose gel electrophoresis.

Restriction and ligation of the vectors and PCR products proceed in accordance with the enzyme manufacturer's standard protocol. In-gel ligation is performed in accordance with the low-melting agarose manufacturer's protocol (Seaplaque GTG, FMC). The manufacturers' instructions are taken into account for use of the restriction endonucleases, the alkaline phosphatase and T4 DNA ligase (Pharmacia). The Glass Max System (Gibco BRL) is used to purify DNA fragments. Correct insertion of the PCR amplification products is confirmed by molecular weight determination by means of agarose gel electrophoresis and by partial DNA sequencing.

The *Treponema pallidum* antigens are then expressed. The applied cloning strategy using the plasmid vector pQE-30 results in expression systems for recombinant *Treponema pallidum* antigens which are characterised as follows: after a promoter/operator element consisting of the bacteriophage T5 promoter, two lac operator sequences and a synthetic ribosomal binding site (Stüber et al., in Lefkovits/Pernis, *Immunological Methods*, volume IV, 121–152 (1990)), there follow the start codon, sequences for 6 successive histidine residues, a polylinker to insert protein-coding sequences and a vector-coded transcription terminator. When expression vector pQE-30 is used, the recombinant proteins are modified by an N-terminal hexahistidine sequence. The lactose repressor to control gene expression is coded on plasmid pREP4, two or more copies of which are present in host strain M15, and is selected by means of the kanamycin-resistance thereof. The synthetic lactose derivative IPTG is beeing used as the inducer of gene expression.

Figure 2:
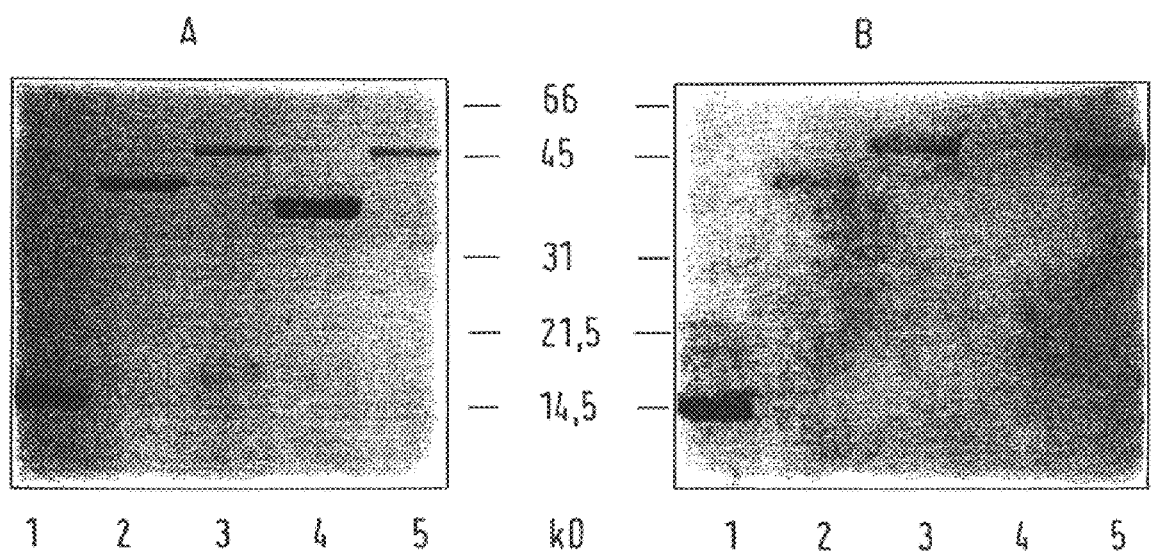
FIGS. 2A–2B a Coomassie dyed gel and a western immunoblot with recombinant antigens.

FIG. 2 shows the expression and immunoreactivity of the recombinant fusion proteins 17 kD antigen, 47 kD antigen, BMP, TmpA, TmpC. The recombinant antigens are expressed by culturing bacteria of strain M15 with the corresponding recombinant plasmids and inducing gene expression by adding 2 mM of IPTG during the logarithmic growth stage. After three hours' further incubation, the cells are harvested, the fusion proteins purified by means of Ni-NTA-Sepharose and separated by SDS-PAGE. A distinct protein band may be made visible for each of the fusion proteins in Coomassie-dyed gel (left hand side of the image).

In the western blot (right hand side of the image), the corresponding clones exhibit immunoreactivity of the recombinant proteins 17 kD antigen (column 1), BMP (column 2), 47 kD antigen (column 3) and TmpA (column 5). No immunoreactivity is detectable for TmpC (column 4).

Strong gene expression is detected after only one hour for all the constructed expression systems, with the exception of the 15 kD antigen. The subsequent purification is performed using cultures which have been induced for three hours with 2 mM of IPTG. The expected molecular weight is confirmed by SDS-PAGE and Coomassie dyeing and the western blot substantiates the reactivity of the recombinant antigens with syphilis serum (FIG. 2). A clearly discernible band is present for each of the 47 kD antigen, the 17 kD antigen, BMP and TmpA. The 17 kD antigen exhibits a further very weak immunoreactive band having a molecular weight of 35 kD which may be attributable to dimerisation. TmpC exhibits no immunoreactivity and the 34 kD antigen only slight immunoreactivity.

The six successive histidine amino acid residues of the recombinant fusion protein allow the antigens to be purified using the principle of immobilised metal chelate affinity chromatography (Hochuli et al., *J. Chromatogr.* 411, 177–184 (1987)). The chelate ligand used, NTA (nitrilotriacetic acid), has four binding sites which occupy four of the six possible bonds of the complexing nickel ion. The chelate ligand bearing metal ions (Ni-NTA, Hoffmann-La Roche) is immobilised on Sepharose CL-6B. The remaining two binding sites of the nickel ion react with the 6×histidine affinity end on the N-terminal end of the recombinant protein. The recombinant proteins are eluted by protonation of the histidine amino acid residues in the acidic pH range (at approx. pH 5.8) and dissociation of the Ni-NTA ligands. The recombinant *Treponema pallidum* antigens are purified in accordance with the manufacturer's protocol (QIAGEN, see above) from the centrifuge pellet from 500 ml of induced bacterial culture under denaturing conditions. The yield is between 5 and 68 mg of protein/liter of induced culture. Purity, determined by densitometry, varies between 70 and 99%.

The binding of *Treponema pallidum* antigen to a solid phase and the detection of specific antibodies are discussed in the following Examples.

WORKING EXAMPLES

Example 1

Adsorptive Binding of Recombinant *Treponema Pallidum* Antigen to Microtitre Plates and Calorimetric Enzyme Immunoassay (col. EIA)

Microtitre plates of moderate binding capacity (F-Form, Greiner) are loaded for 18 hours at 4° C. with 100 μl of antigen in 0.1 M bicarbonate buffer (0.04 M $Na_2CO_3$, 0.06 M $NaHCO_3$, pH 9.6). Antigen concentration was 1 μg/ml. The loaded plates were washed three times with 200 μl of washing buffer (PBS, 0.05% Tween 20) in order to remove any unbound antigen. The free binding sites on the plastic surface of the microtitre plate were then blocked with 5% skim milk powder in washing buffer for 1 hour and washing was then performed three times. Incubation was then performed for two hours with 100 μl of patient serum in washing buffer at various dilutions. Three washing stages with 200 μl portions of washing buffer then followed. An anti-human IgG/AP conjugate (γ chain specific) was then diluted in washing buffer in accordance with the manufacturer's instructions (SIGMA). 100 μl portions of conjugate were filled into the wells of the microtitre plate and incubated for 2 hours at room temperature. After washing three times, 200 μl of the enzyme substrate p-nitrophenyl phosphate in 0.2 M Tris (p-NPP substrate tablet set, SIGMA) were then added and incubated in the dark at room temperature. After 30 minutes, the reaction was terminated by adding 50 μl of 3 N NaOH. Absorbance was measured against the substrate blank at a wavelength of 405 nm in an Anthos microtitre plate photometer.

Figure 4:
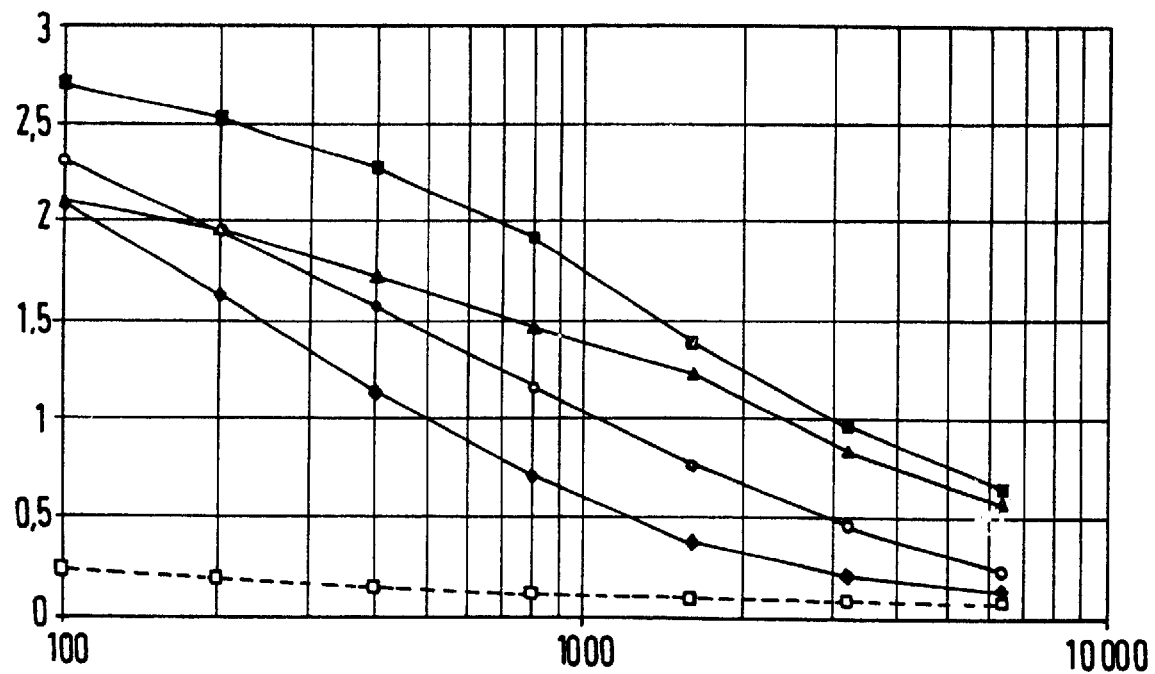
FIG. 4 a calorimetric ELISA to show the dependency of absorbance on serum dilution.

The assay was optimised by performing chequerboard titrations and a 1:4000 dilution of the secondary antibody and a 1:400 dilution of the serum were selected as standard conditions (FIGS. 3 and 4). At higher dilutions, a reduction in the quotient of absorbance of a pooled secondary syphilis serum and a negative serum (P/N quotient) was observed. The highest P/N quotients of 17.1, 7.4 and 11.7 were determined for the 17 kD antigen, the 47 kD antigen and TmpA. These three antigens were accordingly selected for a combined ELISA.

FIG. 4 shows serum dilution as the x coordinate and absorbance at 405 nm as the y coordinate. The figure shows the dependency of absorbance values in the calorimetric ELISA on serum dilution after separate loading of the microtitre plates (in each case at 1 μg/ml). The lowermost curve, marked with rectangular boxes, is a negative pool above which (in this order) are the curves for 47 kD antigen, TmpA, 17 kD antigen and for simultaneous loading with these three recombinant antigens (each 1 μg/ml).

Example 2

Adsorptive Binding of Recombinant *Treponema Pallidum* Antigens onto Microtitre Plates and Chemiluminescent Enzyme Immunoassay (CL-EIA)

The following protocol was developed on the basis of the ELISA-Light Kit (Tropix Inc., USA), the detection system of which is based on chemiluminescence on the enzymatic conversion of dioxetanes (EP 0 275 260 B1):

Microtitre plates (Mikrolite®, Dynatech USA) are loaded under the conditions stated in Example 1 (antigen solution 1 μg/ml in bicarbonate buffer) and washed three times after 18 hours' incubation at 4° C. (PBS, 0.05% Tween 20). After 1 hour's blocking (PBS, 0.5% I-Block [Tropix Inc.], 0.05% Tween 20), washing is performed four times with washing buffer (0.2% I-Block, 0.05% Tween 20 in PBS). Subsequent incubation with patient sera diluted in washing buffer lasts for a period of one hour. Three washing steps are followed by one hour's incubation with anti-human IgG/AP conjugate (γ chain specific, SIGMA) diluted 1:2500 in washing buffer. Washing is then performed three times with washing buffer and twice with assay buffer (0.1 M diethanolamine, 1 mM MgCl$_2$, pH 10.0). Incubation is then performed for 10 minutes with 100 μl of enhancer/substrate (assay buffer, 10% Sapphire, 0.2 mM CSPD [both from Tropix Inc.]). Chemiluminescence is measured after 20 minutes in a Lucy1 microtitre plate luminometer (Anthos).

The assay was optimised by performing chequerboard titrations and a 1:2500 dilution of the secondary antibody and a 1:800 dilution of the serum were selected as the standard conditions.

Figure 5:
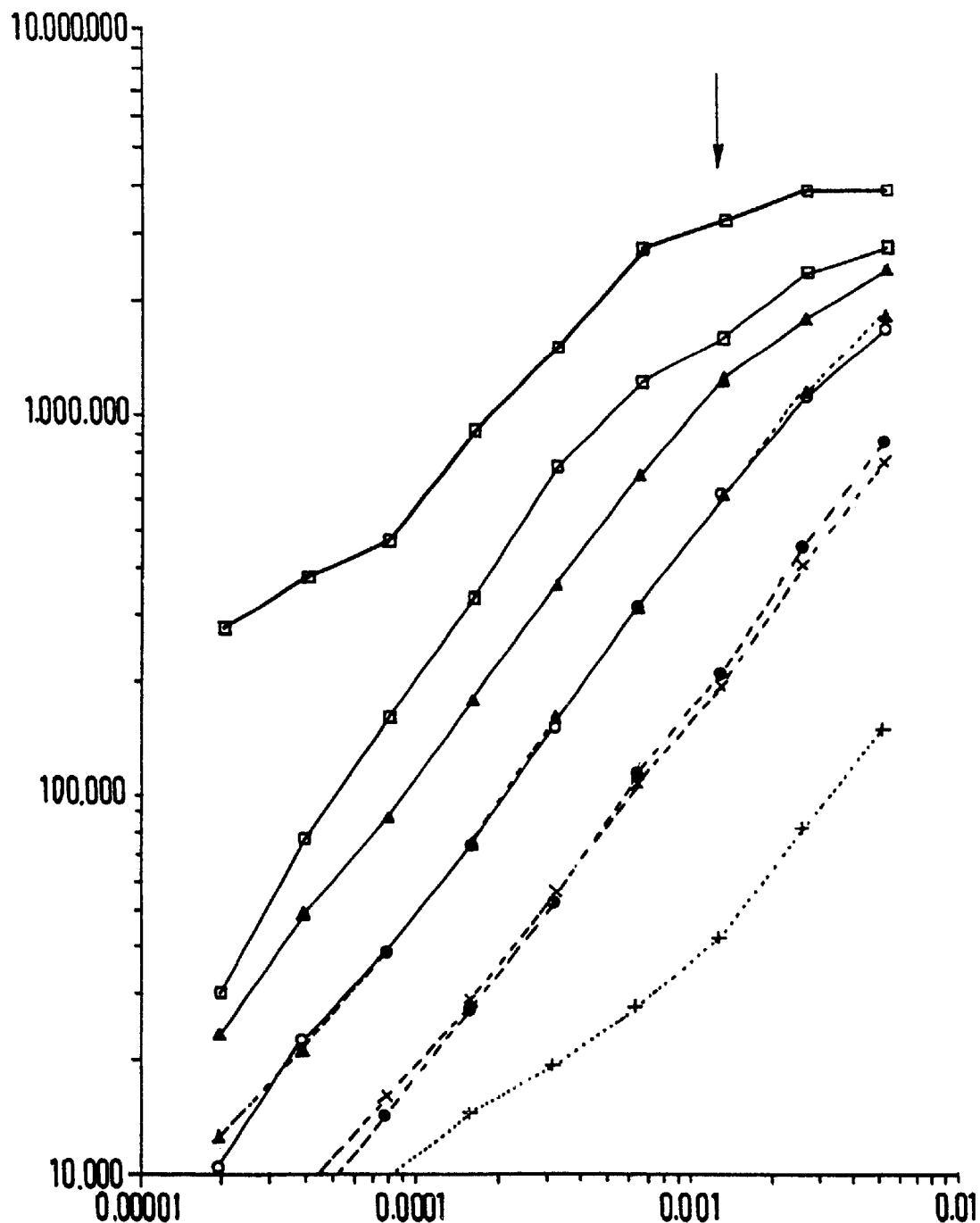
FIG. 5 a chemiluminescent ELISA to show the dependency of chemiluminescence on serum dilution.

FIG. 5 shows the dependency of intensity of chemiluminescence (in counts per second, plotted on the y-axis) upon antibody concentration (plotted as serum dilution on the x-axis) to the individual antigens and antigen combination TmpA, 47 kD antigen and 17 kD antigen (tested on dilutions from the pooled secondary syphilis serum). From the top downwards, the curves show the chemiluminescent EIA (CL-EIA) of the stated antigen combination, of 17 kD antigen, TmpA, BMP, 47 kD antigen, 34 kD antigen, TmpC and Tp4. The curve is virtually linear over a six-fold change in titre. The corresponding curves are highly suitable as reference curves for the quantitative determination of antibody concentrations in unknown test specimens. The wide linear range demonstrates the superiority of the chemiluminescent EIA for quantitative antibody determinations in comparison with calorimetric detection.

The standard dilution of 1:800 is marked with an arrow.

Figure 6:
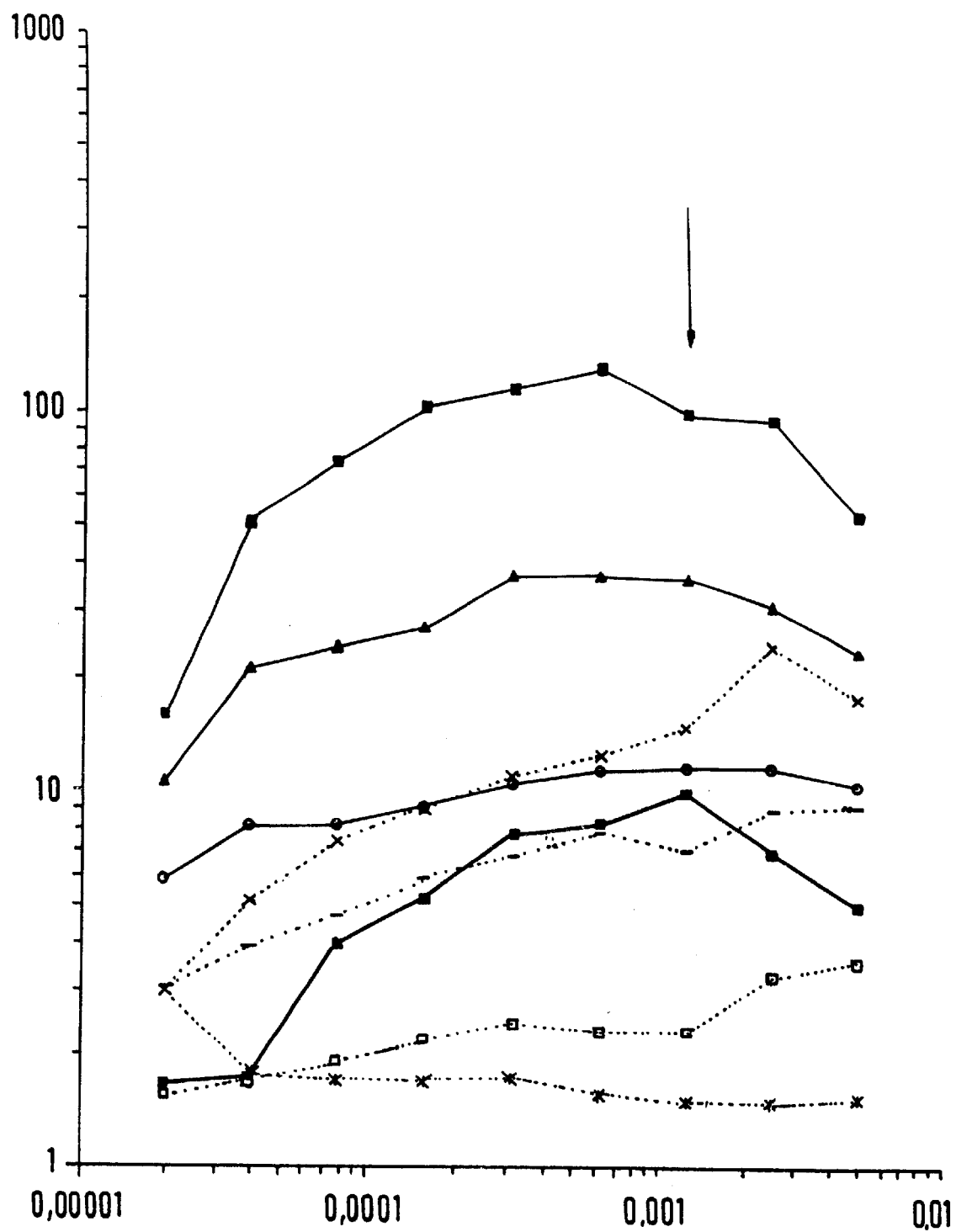
FIG. 6 a chemiluminescent ELISA to show the dependency of the positive/negative quotient on serum dilution.

FIG. 6 shows the positive/negative quotients in the chemiluminescent EIA plotted on the y-axis against serum dilution on the x-axis. In this case too, the arrow indicates the standard dilution of 1:800. The sequence of the curves in this case (from the top at 1:800) is: 17 kD antigen CL-EIA, TmpA, BMP, 47 kD antigen, antigen combination (as before), 34 kD antigen, TmpC, Tp4. This quotient allows further conclusions to be drawn concerning the diagnostic use of the recombinant proteins.

The chemiluminescent assays with Tp4 and TmpC are, however, not suitable for use in serological syphilis diagnostics as the antibody concentrations, measured from the level of chemiluminescence, and the P/N quotients (1.5; 2.2) are too low. Due to the comparatively low P/N quotient of 6.7, the 34 kD antigen is less suitable for diagnostic use. The highest chemiluminescence values were measured in the corresponding chemiluminescent EIAs for the 17 kD antigen, TmpA, the 47 kD antigen and BMP. The P/N quotients were 94 for the 17 kD antigen, 35 for TmpA, 11 for the 47 kD antigen and 14 for BMP (serum dilution 1:800, FIG. 6).

Sera from patients at various stages of syphilis were investigated using the 17 kD CL-EIA, the TmpA CL-EIA, the 47 kD CL-EIA and the BMP CL-EIA and CL-EIA having the combination of 17 kD antigen, 47 kD antigen and TmpA. The chemiluminescence values are here converted to a multiple of a concurrently investigated pooled negative serum. The results are shown in FIG. 7. The limit value set for qualitative evaluation of the assay is three times the standard deviation from the blood donor mean (n=38).

Table 2 at the end of the description compares the results from the chemiluminescent EIA, together with the results from the colorimetric assay, with the results from CMT, the TPHA test and the FTA-ABS test. The sera tested were from patients with primary syphilis (LI), secondary syphilis (LII), tertiary syphilis (LIII), latent syphilis (LLa). The results from the colorimetric assay (col. EIA) were stated in absorbance units, those for the chemiluminometric assay (CL-EIA) in relative units (as a multiple of the chemiluminescence of a negative reference serum). Sera below the defined limit value (mean plus three standard deviations from 37 to 42 blood donor sera) are indicated. Overall, the results are found to correlate, in that low antibody concentrations are detected in the enzyme immunoassay in sera having a low titre in the CMT, TPHA or FTA-ABS tests. This is particularly clear for the sera from the latent stage of syphilis. In the BMP CL-EIA, 8 of 18 sera are below the limit value, including all the sera investigated in the latent stage of syphilis. On the basis of the results obtained to date, isolated detection of antibodies to BMP is not suitable for serological screening for syphilis. The initial findings presented here do, however, allow one to conclude that there is a possible correlation between antibody concentrations and the stage and/or activity of the disease. Should this be confirmed once a larger number of syphilis patients have been tested, detection of an antibody to BMP could be usable, for example, for monitoring treatment. Of the 18 syphilis sera investigated, two each are negative in the CL-EIAs with the 17 kD antigen and the 47 kD antigen, while three sera are negative with TmpA. Of these, one serum is negative in all three tests, while the other negative findings in one assay with recombinant antigen are associated with positive findings for the other recombinant antigens. It may be concluded from this that adequate diagnostic reliability may only be achieved by determining antibodies to two or more recombinant antigens.

Example 3

Covalent Binding of Recombinant *Treponema Pallidum* Antigen and Chemiluminescent Enzyme Immunoassay Super-paramagnetic polystyrene particles (DYNA BEADS M-280, tosyl-activated, DYNAL Norway) are used to bind recombinant *Treponema pallidum* antigens covalently to a solid phase. The principle of covalent binding has been adequately described in the technical documentation. A further essential component of this method is the principle of separating the particles from their reaction solutions with a magnetic field. In the present Example, Eppendorf tubes containing the magnetic particles in the reaction solution are placed in a magnetic separator for phase separation. In the separator, the super-paramagnetic particles are drawn to the wall by the magnetic field of a permanent magnet and the reaction solution may then be removed with a pipette or by suction.

The test was performed by way of example using the recombinant 17 kD antigen. The particles were separated from the transport medium in the magnetic separator, resuspended to 20 mg/ml, combined with an identical volume of recombinant protein and incubated for 24 hours at 37° C. with shaking. The reaction conditions during the consequent binding of the recombinant protein to the particles were: 10 mg/ml of particles, 20 µg/ml of recombinant protein in 0.05 M borate buffer pH 9.5. Washing was then performed with washing buffer (PBS, 0.2% I-Block, 0.05% Tween 20), three times for 10 minutes, once for 30 minutes and once overnight, wherein free protein binding sites were simultaneously blocked. The loaded particles were stored at 4° C. and washed twice with washing buffer on the day of assay and divided into portions for the test batches. In one assay, 0.05 mg of particles were incubated for 1 hour at 37° C. with 100 µl of patient serum at a dilution of 1:800 in washing buffer. After washing twice, incubation was performed for 1 hour with secondary antibodies (1:2500 anti-human alkaline phosphatase conjugate, γ chain specific, SIGMA). Washing was then performed twice in washing buffer and twice in diethanolamine buffer (0.1 M diethanolamine, 1 mM $MgCl_2$, 0.02 $NaN_3$, pH 10.0). Once the particles had been resuspended in 50 µl of diethanolamine buffer, they were transferred into microtitre plates, each well containing 50 µl of enhancer/substrate solution. (Final concentration in 100 µl: 10% Sapphire, 0.2 mM CSPD [both from Tropix Inc.]). The chemiluminescence mediated by the alkaline phosphatase from the reaction of the substrate was measured in a Lucy1® microtitre plate luminometer (Anthos). In this system with the 17 kD antigen, a pooled serum from 73 blood donors was compared with a pooled serum from patients with secondary syphilis. At an integration time of 1 s per chemiluminescence measurement, the following relative counts were obtained for the pooled syphilis serum 1,481,958.5 (10 minutes after the beginning of the reaction), 1,641,317.5 (after 20 minutes) and 1,746,169 (after 30 minutes) and for the pooled blood donor serum 7,519.5 (after 10 minutes), 9,929.5 (after 20 minutes) and 11,629 (after 30 minutes). This corresponds to a positive/negative quotient of 197 after 10 minutes' incubation of the substrate, of 165 after 20 minutes and 150 after 30 minutes. It is evident from these values that a lesser, non-specific binding of antibodies to the solid phase clearly occurs. Analytical sensitivity is accordingly superior to the systems proposed in Example 1 and Example 2.

Simultaneous use of recombinant antigens in serological diagnostics thus improves capability. In infectious disease serodiagnostics, detection of different antibody specificities to the causal agent in principle allows an improvement in sensitivity in comparison with detection of antibodies to a single antigen. For this reason, a western immunoblot is used, for example, as a confirmatory test in HIV diagnostics. In such tests, antibodies from the test specimen react with material from the pathogen, the antigens of which are separated by electrophoresis and transferred onto a solid phase. The test may be deemed certainly positive if two or more causal agent-specific bands are reactive. Detection of different antibody specificities is essential to diagnosis if antibodies to individual antigens cannot be detected in all those suffering from the disease.

The present invention proposes a mixed antigen ELISA which, in the event of insufficient reactivity of the serum to one or more antigens, provides a positive test outcome by detection of antibodies to the other antigens. Investigation of syphilis patient sera using the calorimetric system (Example 1) and the chemiluminescence assay (Example 2) revealed that individual sera provided a negative reaction in the single antigen ELISA (Table 2). One serum exhibited negative test results in the enzyme immunoassay with TmpA, BMP, 47 kD antigen and 17 kD antigen using both the colorimetric detection system and chemiluminescent detection. An explanation is provided by the western blot with *Treponema pallidum* whole antigen which exhibited clear reactivity only for Tp4. A chemiluminescent ELISA with recombinant Tp4 was also strongly positive for this serum. Since Tp4 is known to be immunologically cross-reactive with Hsp60 proteins from other species of bacteria, isolated detection of antibodies to Tp4 is of little diagnostic value and could also be attributable to another infection. The other sera giving a negative test result in the single antigen ELISA, however, exhibited positive results with the other recombinant antigens tested. The mixed antigen ELISA was positive in these cases. This substantiates the superiority of a mixed antigen ELISA with recombinant antigens over single antigen ELISAs for the qualitative detection of a syphilis infection. Combined use of recombinant antigens to detect a syphilis infection is accordingly an essential feature of the present invention.

Figure 8:
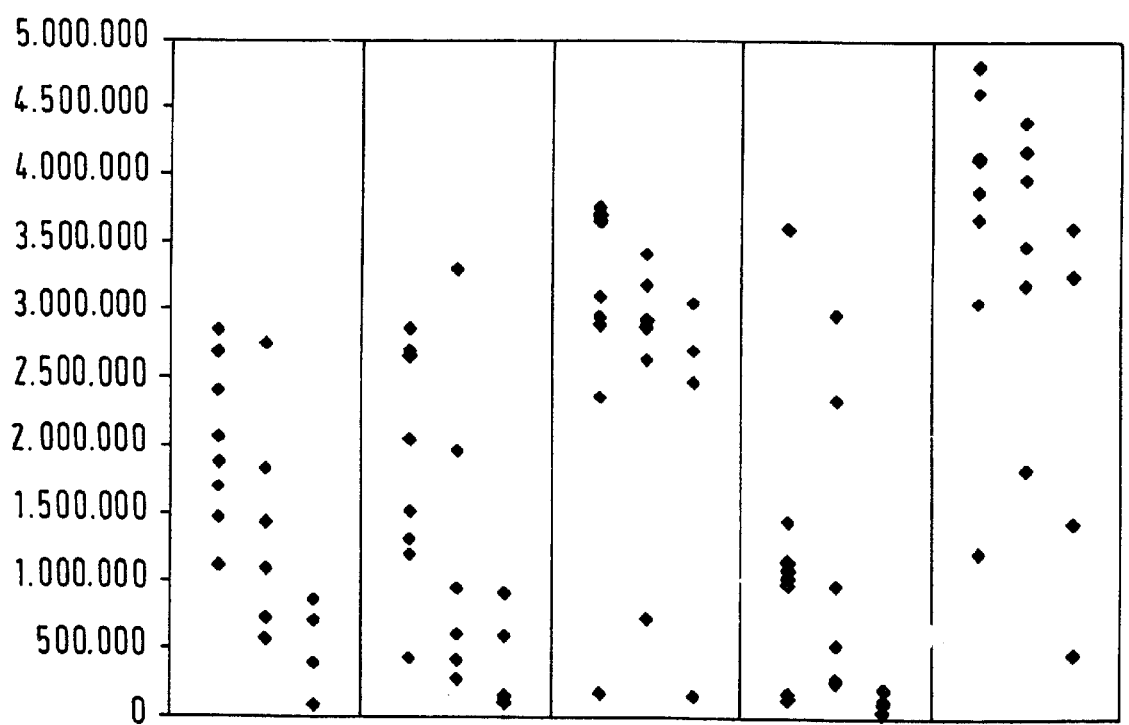
FIG. 8 a chemiluminescent ELISA to detect antibodies to Treponema pallidum at various stages of syphilis.

In the single antigen ELISA, the measured counts for highly positive sera were at approximately the same level (FIG. 8), such that the microtitre plates were simultaneously loaded with identical concentrations of the antigens. In a test for the simultaneous detection of antibodies to two or more recombinant antigens, it is vital that each generates a measurable proportion of the total signal. The effectiveness with which the recombinant antigens are bound to the solid phase may, however, be variable. Competitive effects may also play a part in antigen/antibody reactions with two or more antigens which are bound to the same support. A test was accordingly performed in which recombinant antigen was added to the patient serum. The corresponding antibodies thus react with the recombinant antigen in solution and not with that bound to the solid phase. The effectiveness of this competitive inhibition was determined for each antibody specificity in the single antigen ELISA and was between 91 and 99%. This elevated percentage meant that the inhibitory effect measured in the mixed antigen ELISA could be used to provide an approximate estimate of the proportion of CL for the antibody binding to the individual antigen. Thus, for a pooled serum from patients with secondary syphilis, the proportion of chemiluminescence in the mixed antigen ELISA (loading concentration 1 µg/ml each) caused by antibodies to the 17 kD antigen could be estimated at 52%, that caused by TmpA antibodies 43, and antibodies to the 47 kD antigen 5%. Detection of antibodies to the 47 kD antigen is apparently under-represented. Since the 47 kD antigen is a specific *Treponema pallidum* antigen with strong immunogenicity, the desired proportion of the total signal should be modified by modifying the concentration ratios of the recombinant antigens during loading and tested as described.

The use of microparticles is an elegant method for the simultaneous detection of antibody specificities. Each individual recombinant antigen is bound to the microparticles in a separate batch and the chemiluminescence values determined in the test with single antisera. The resultant values may be used to determine an optimum mixing ratio for the microparticle preparations, such that a measurement above the limit value (cut off) is achieved for the largest possible number of syphilis patients. If microparticles are separately loaded with antigen and only subsequently mixed, competitive inhibition effects are excluded both during antigen binding to the solid phase and during the antigen/antibody reaction. The feasibility and superiority of this approach is sufficiently substantiated by the ELISAs of Example 2, Example 3 and the mixed antigen ELISA (microtitre plate method). The described method is suitable for binding antigen, antigen constituents or also peptides with selected antigen determinants to microparticles, for determining the diagnostic relevance thereof and the combined use thereof for a qualitative test in syphilis serodiagnostics. Other infectious diseases may possibly be diagnosed using this method if the diagnostically relevant antigens of the causal agent concerned are deemed appropriate.

The method in which different recombinant antigens separately bound to microparticles as the solid phase are evaluated against diagnostic criteria in test systems, and in which these microparticles are then used in an optimum mixture ratio in a qualitative serological test, is particularly advantageous.

This invention relates to an immunochemical method for detecting and determining antibodies to *Treponema pallidum* in the blood serum and other body fluids. The described detection method is based upon the quantitative detection of antibodies to recombinant *Treponema pallidum* antigens, wherein each individual antigen or combinations thereof is/are detected. The proposed method allows a comparison of the incidence and titre of antibodies to each *Treponema pallidum* antigen in syphilis patients in comparison with uninfected patients. Conclusions may be drawn from this comparison with regard to the diagnostic relevance of the detection of antibodies to each invested antigen. Antibody titres for each individual antigen are dependent upon the stage of the disease and exhibit individual variations. It is described how the combined use of two or more recombinant antigens in a test method may bring about improved diagnostic sensitivity and specificity. The method of purposeful, combined detection of antibodies to selected antigens for the serological diagnosis of syphilis is a constituent part of this invention. Such test systems are described. Use of the described methods results in a new generation of test systems for serological detection of syphilis infections on the basis of recombinant *Treponema pallidum* antigens.

TABLE 1

| Sequence identifier | Pimer Sequence | for gene amplification of antigen (designation* referred to S. J. Norris, Microbiological Reviews, Sept. 1993, p. 750–779) | | first codon for antigen specific aminoacid | added restriction site | Comment |
|---|---|---|---|---|---|---|
| SEQ ID NO: 1 | ATAATA GGA TCC TGT GTC TCG TGC ACA ACC GTG | 17 kD antigen | (= TpN17*) | TGT | BamHI | 5' primer without leader sequence |
| SEQ ID NO: 2 | AGAGACGTGGAC CTA TTT CTT TGT TTT TTT GAG | 17 kD antigen | (= TpN17*) | | Sa1I | 3' primer with stop codon |
| SEQ ID NO: 3 | TATTAT GGA TCC TGC TCT AAG AGC GAC AGG CC | TmpC | (= TpN35*) | TGC | BamHI | 5' primer without leader sequence |
| SEQ ID NO: 4 | AGAGACGTCGAC TTA GTT CAT CAT GCG TGC AGA | TmpC | (= TpN35*) | | Sa1I | 3' primer with stop codon |
| SEQ ID NO: 5 | TAATAT GGA TCC TGT GCC TCG GGC GCC AAG GAG | TmpA | (= TpN44.5*) | TGT | BamHI | 5' primer without leader sequence |
| SEQ ID NO: 6 | ATGATAGTCGAC TCA TCG AGA GGC TCC TTC TTC | TmpA | (= TpN44.5*) | | Sa1I | 3' primer with stop codon |
| SEQ ID NO: 7 | TATTAT GGA TCC CAG TCG GCG CTG CAG CCT ATC | BMP | (= TpN39(b)*) | CAG | BamHI | 5' primer without leader sequence |
| SEQ ID NO: 8 | TATTATGTCGAC TCA CCA GTC GAG CAC CTT GCC | BMP | (= TpN39(b)*) | | Sa1I | 3' primer with stop codon |
| SEQ ID NO: 9 | TAAGAC GGA TCC TGT GGC TCG TCT CAT CAT GAG | 47 kD antigen | (= TpN47*) | TGT | BamHI | 5' primer without leader sequence |
| SEQ ID NO: 10 | TATTAGGTCGAC CTA CTG GGC CAC TAC CTT CGC | 47 kD antigen | (= TpN47*) | | Sa1I | 3' primer with stop codon |
| SEQ ID NO: 11 | TTATCT GGA TCC TGC GGG GGC GGT GGA GAG CAT CAG | 34 kD antigen | (= TpN29–35) | TGC | BamHI | 5' primer without leader sequence |

TABLE 1-continued

| Sequence identifier | Pimer Sequence | for gene amplification of antigen (designation* referred to S. J. Norris, Microbiological Reviews, Sept. 1993, p. 750–779) | | first codon added for antigen specific aminoacid | restriction site | Comment |
|---|---|---|---|---|---|---|
| SEQ ID NO: 12 | CGGCTA AGA TCT CTA CCA CTG AGG CCC CTT CCA TTC | 34 kD antigen | (= TpN29–35) | | BglII | 3' primer with stop codon |
| SEQ ID NO: 13 | TACAT GGA TCC AAG AGG GTG AGT TTG CTC GGG AG | 34 kD antigen | (= TpN29–35) | AAG | BamHI | 5' primer without leader sequence |
| SEQ ID NO: 14 | ACCACA GGA TCC TGT TCA TTT AGT TCT ATC CCG | 15 kD antigen | (= TpN15) | TGT | BamHI | 5' primer with leader sequence |
| SEQ ID NO: 15 | GAGCGAGTCGAC CTA CCT GCT AAT AAT GGC TTC CTT | 15 kD antigen | (= TpN15) | | SaII | 3' primer with stop codon |
| SEQ ID NO: 16 | CACAGC GGA TCC GCG AAC GAA TTG CTG TTT AAT | Tp4 | (= TpN60) | GCG | BamHI | 5' primer without leader sequence |
| SEQ ID NO: 17 | GAGAGTGTCGAC TCA ATA CAT ACC TCC CAT ACC | Tp4 | (= TpN60) | | SaII | 3' primer with stop codon |

TABLE 2

| Serum | CMT (titre) | TPHA (titre) | FFA-ABS (titre) | 17 kD Ag col. EIA | 17 kD Ag CL EIA | TmpA col. EIA | TmpA CL EIA | 47 kD Ag col. EIA | 47 kD Ag CL EIA | BMP CL EIA | 3 Ag mix 17, 47, Tmp col. EIA | 3 mix 17, 47, Tmp CL EIA |
|---|---|---|---|---|---|---|---|---|---|---|---|---|
| LI-2 | 64 | 5120 | 5 | 1.40 | 15.69 | 0.92 | 23.22 | 1.79 | 25.5 | 1.38 | 1.31 | 9.09 |
| LI-3 | 64 | 5120 | 10 | 2.34 | 24.51 | 2.42 | 38.91 | 2.07 | 33 | 27.96 | 2.14 | 13.68 |
| LI-4 | 8 | 160 | 5 | 0.12 | 1.17 | 0.86 | 15.27 | 0.41 | 5.4 | 1.08 | 0.83 | 3.63 |
| LI-5 | 64 | 20480 | 80 | 2.42 | 19.17 | 2.78 | 32.88 | 2.47 | 33.6 | 7.56 | 2.08 | 12.27 |
| LI-6 | 32 | 40960 | 160 | 2.42 | 20.64 | 1.62 | 20.07 | 1.45 | 18.9 | 11.25 | 2.07 | 10.92 |
| LI-7 | 64 | 5120 | 80 | 1.04 | 24.24 | 1.57 | 28.2 | 0.43 | 14.88 | 7.95 | 2.59 | 12.21 |
| LI-8 | 32 | 2560 | 160 | 2.49 | 19.56 | 2.62 | 36.6 | 1.57 | 16.35 | 8.91 | 2.69 | 11.52 |
| LI-9 | 64 | 655280 | 320 | 3.43 | 24.99 | 3.03 | 25.68 | 2.57 | 35.64 | 8.52 | 3.44 | 14.31 |
| LII-1 | 16 | 327680 | 5 | 2.44 | 19.44 | 0.24 | 7.74 | 0.53 | 3.48 | 2.01 | 1.49 | 10.35 |
| LII-2 | 64 | 20480 | 160 | 0.48 | 4.83 | 0.59 | 14.97 | 0.77 | 7.53 | 2.19 | 1.12 | 5.46 |
| LII-3 | 4 | 81920 | 5 | 2.32 | 19.11 | 0.58 | 9.93 | 0.37 | 5.25 | 4.14 | 1.54 | 9.48 |
| LIII-4 | 64 | 163840 | 5 | 2.32 | 17.46 | 1.76 | 19.56 | 1.36 | 11.85 | 18.12 | 1.73 | 11.79 |
| LII-5/6 | 64 | 5120 | 640 | 1.84 | 21.18 | 2.54 | 37.5 | 2.03 | 41.07 | 7.59 | 2.34 | 12.42 |
| LII-8 | 32 | 81920 | 5 | 2.32 | 22.68 | 2.04 | 24.99 | 1.40 | 24.45 | 23.04 | 2.31 | 13.05 |
| LIII | 16 | 10240 | 5 | 2.06 | 17.91 | 0.48 | 11.82 | 0.40 | 11.37 | 1.65 | 1.42 | 10.74 |
| LLa-2 | 1 | 2560 | n.d. | 1.53 | 16.41 | 0.27 | 5.37 | 0.12 | 1.92 | 0.96 | 0.94 | 4.29 |
| LLa-3 | 4 | 10240 | 10 | 2.22 | 20.28 | 0.74 | 9.6 | 0.68 | 7.38 | 0.78 | 1.34 | 9.66 |
| LLa.4 | 2 | 2560 | 5 | 0.20 | 1.02 | 0.19 | 1.14 | 0.14 | 1.26 | 0.3 | 0.27 | 1.41 |
| | | | | 17kD | 17kD | TmpA | TmpA | 47kD | 47kD | BMP | 3 mix | 3 mix |
| Reactive sera | | | | 16/18 | 16/18 | 15/18 | 17/18 | 16/18 | 16/18 | 10/18 | 17/18 | 17/18 |
| Limit value (3 st. dev. range) | | | | 0.25 | 2.27 | 0.33 | 2.8 | 0.22 | 2.77 | 2.43 | 0.36 | 3.4 |

What is claimed is:

1. A method for the detection of antibodies to *Treponema pallidum*, comprising the steps of:
   gene-amplifying and cloning a selection of recombinant antigens,
   expressing the gene-amplified and cloned antigens in host vector systems,
   purifying the expressed antigens,
   binding the purified antigens to a solid phase individually or in combination,
   subjecting the bound antigens to a reaction with a clinical specimen, and
   using a detection system to determine the antibodies bound from the clinical specimen by means of an antigen/antibody reaction,
   wherein the selection of the recombinant antigens for detecting antibodies to *Treponema pallidum* consists of 17 kD antigen, 47 kD antigen and Treponemal membrane protein A (TmpA).

2. The method of claim 1, further comprising the step of: amplifying a coding DNA for the selection of the recombination antigens by polymerase chain reaction.

3. The method of claim 1, further comprising the steps of inserting an amplified DNA in plasmid vector pQE-30 and expressing the amplified DNA in *E. coli* M15.

4. The method of claim 1, further comprising the step of purifying the recombinant antigens by affinity chromatography.

5. The method of claim 1, further comprising the step of binding the recombinant, purified antigens to the solid phase by one of the group consisting of adsorptive binding, covalent binding, and via a ligand already bound to the solid phase.

6. The method of claim 1, wherein the clinical specimen includes a body fluid selected from the group consisting of blood serum, spinal fluid, ascites, amniotic fluid, and combinations thereof.

7. The method of claim 1, further comprising the step of using secondary labeled antibodies to detect the antibodies to *T. pallidum* present in the clinical samples.

8. The method of claim 7, further comprising the step of labeling the secondary antibodies by using any one of the labels from the group consisting of fluorescent dye, radioisotope, enzyme, or combinations thereof.

9. The method of claim 8, wherein the secondary antibody is labeled via bound ligands.

10. The method of claim 1, wherein detection in the detection system is selected from the group consisting of color development, chemiluminescence, fluorescence, radioactivity, or combinations thereof.

11. The method of claim 1, further comprising the step of simultaneously binding two or more of said recombinant antigens to the solid phase.

12. The method of claim 1, further comprising the step of binding each of said recombinant antigens separately to a separate solid phase, and using each solid phase together in the test.

13. An agent prepared from recombinant antigens for performance of the method of claim 1 for the detection of antibodies to *Treponema pallidum*, said agent consisting of 17 kD antigen, 47 kD antigen, and Treponemal membrane protein A (TmpA).

14. The method of claim 1, further comprising the step of performing the detection of antibodies using one of the group consisting of qualitative detection, quantitative detection, and combinations thereof.

15. The method of claim 9, further comprising the step of directly labeling the secondary antibody.

16. The method of claim 9, further comprising the step of indirectly labeling the secondary antibody.

17. A method for the detection of antibodies to *Treponema pallidum*, comprising the steps of:

gene-amplifying and cloning a selection of recombinant antigens, expressing the gene-amplified and cloned antigens in host vector systems, purifying the expressed antigens, binding the purified antigens to a solid phase individually or in combination, subjecting the antigens bound to the solid phase to a reaction with a clinical specimen, and using a detection system to determine the antibodies bound from the clinical specimen by means of an antigen/antibody reaction, wherein the selection of the recombinant antigens for detecting antibodies to *Treponema pallidum* consists of 17 kD antigen, 47 kD antigen, Treponemal membrane protein A (TmpA), and combinations of 34 kD antigen, Treponemal membrane protein C (TmpC), *Treponema pallidum* Basic Membrane Protein (BMP), and bacterial Common Antigen of *Treponema pallidum* (Tp4).

18. An agent prepared from recombinant antigens for the performance of a method for the detection of antibodies to *Treponema pallidum*, said agent consisting of 17 kD antigen, 47 kD antigen, TmpA, and combinations of 34 kD antigen, TmpC, BMP, and Tp4.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
    (A) LENGTH: 33 bases
    (B) TYPE: nucleic acid
    (C) STRANDEDNESS: single
    (D) TOPOLOGY: linear (ii) MOLECULE TYPE: other nucleic acid
    (A) DESCRIPTION: synthetic oligonucleotide with partial
        homology to genomic T.

(iii) HYPOTHETICAL: no (iv) ANTI-SENSE: no (ix) FEATURE:
            (A) NAME/KEY: 5primer TpN17
            (B) LOCATION: TRP17LPOPR 163-183
            (C) IDENTIFICATION METHOD: partial similarity with known
                sequence
            (D) OTHER INFORMATION: 5primer with an adapter for BamHI (x) PUBLICATION INFORMATION:
            (A) AUTHORS: Gerber, A
                    Krell, S
                    Morenz, J
            (B) TITLE: Recombinant Treponema pallidum antigens in
                    syphilis serology
            (C) JOURNAL: Immunobiology
            (D) VOLUME: 196
            (E) ISSUE: 5
            (F) PAGES: 535-549
            (G) DATE: 1996-1997
            (K) RELEVANT RESIDUES IN SEQ ID NO:1: FROM 1 TO 33

(xi) SEQUENCE DESCRIPTION: SEQ ID NO: 1:

ATAATA GGA TCC TGT GTC TCG TGC ACA ACC GTG                                 33

(2) INFORMATION FOR SEQ ID NO: 2:

(i) SEQUENCE CHARACTERISTICS:
            (A) LENGTH: 33 bases
            (B) TYPE: nucleic acid
            (C) STRANDEDNESS: single
            (D) TOPOLOGY: linear (ii) MOLECULE TYPE: other nucleic acid
            (A) DESCRIPTION: synthetic oligonucleotide with partial
                homology to genomic T.

(iii) HYPOTHETICAL: no (iv) ANTI-SENSE: yes (ix) FEATURE:
            (A) NAME/KEY: 3primer TpN17
            (B) LOCATION: TRP17LPOPR 570-550
            (C) IDENTIFICATION METHOD: partial similarity with known
                sequence
            (D) OTHER INFORMATION: 3primer with an adapter for SalI (x) PUBLICATION INFORMATION:
            (A) AUTHORS: Gerber, A
                    Krell, S
                    Morenz J
            (B) TITLE: Recombinant Treponema pallidum antigens in
                    syphilis serology
            (C) JOURNAL: Immunobiology
            (D) VOLUME: 196
            (E) ISSUE: 5
            (F) PAGES: 535-549
            (G) DATE: 1996-1997

(xi) SEQUENCE DESCRIPTION: SEQ ID NO: 2:

AG AGACGTCGAC CTA TTT CTT TGT TTT TTT GAG                                  33

(2) INFORMATION FOR SEQ ID NO: 3:

(i) SEQUENCE CHARACTERISTICS:
            (A) LENGTH: 32 bases
            (B) TYPE: nucleic acid
            (C) STRANDEDNESS: single
            (D) TOPOLOGY: linear (ii) MOLECULE TYPE: other nucleic acid
            (A) DESCRIPTION: synthetic oligonucleotide with partial
                homology to genomic T.

(iii) HYPOTHETICAL: no (iv) ANTI-SENSE: no (ix) FEATURE:
    (A) NAME/KEY: 5primer TpN35
    (B) LOCATION: TPTMBCL 124-143
    (C) IDENTIFICATION METHOD: partial similarity with known
        sequence
    (D) OTHER INFORMATION: 5primer with an adapter for BamHI (x) PUBLICATION INFORMATION:
    (A) AUTHORS: Gerber, A
        Krell, S
        Morenz, J
    (B) TITLE: Recombinant Treponema pallidum antigens in
        syphilis serology
    (C) JOURNAL: Immunobiology
    (D) VOLUME: 196
    (E) ISSUE: 5
    (F) PAGES: 535-549
    (G) DATE: 1996-1997
    (K) RELEVANT RESIDUES IN SEQ ID NO:1: FROM 1 TO 33

(xi) SEQUENCE DESCRIPTION: SEQ ID NO: 3:

TATTAT GGA TCC TGC TCT AAG AGC GAC AGG CC                         32

(2) INFORMATION FOR SEQ ID NO: 4:

(i) SEQUENCE CHARACTERISTICS:
    (A) LENGTH: 33 bases
    (B) TYPE: nucleic acid
    (C) STRANDEDNESS: single
    (D) TOPOLOGY: linear (ii) MOLECULE TYPE: other nucleic acid
    (A) DESCRIPTION: synthetic oligonucleotide with partial
        homology to genomic T.

(iii) HYPOTHETICAL: no (iv) ANTI-SENSE: yes (ix) FEATURE:
    (A) NAME/KEY: 3primer TpN35
    (B) LOCATION: TPTMBCL 1125-1105
    (C) IDENTIFICATION METHOD: partial similarity with known
        sequence
    (D) OTHER INFORMATION: 3primer with an adapter for SalI (x) PUBLICATION INFORMATION:
    (A) AUTHORS: Gerber, A
        Krell, S
        Morenz, J
    (B) TITLE: Recombinant Treponema pallidum antigens in
        syphilis serology
    (C) JOURNAL: Immunobiology
    (D) VOLUME: 196
    (E) ISSUE: 5
    (F) PAGES: 535-549
    (G) DATE: 1996-1997
    (K) RELEVANT RESIDUES IN SEQ ID NO:1: FROM 1 TO 33

(xi) SEQUENCE DESCRIPTION: SEQ ID NO: 4:

AG AGACGTCGAC TTA GTT CAT CAT GCG TGC AGA                         33

(2) INFORMATION FOR SEQ ID NO: 5:

(i) SEQUENCE CHARACTERISTICS:
    (A) LENGTH: 33 bases
    (B) TYPE: nucleic acid
    (C) STRANDEDNESS: single
    (D) TOPOLOGY: linear (ii) MOLECULE TYPE: other nucleic acid
    (A) DESCRIPTION: synthetic oligonucleotide with partial homology to genomic T.

(iii) HYPOTHETICAL: no (iv) ANTI-SENSE: no (ix) FEATURE:
        (A) NAME/KEY: 5primer TpN44.5
        (B) LOCATION: TRPTMPA 256-276
        (C) IDENTIFICATION METHOD: partial similarity with known
            sequence
        (D) OTHER INFORMATION: 5primer with an adapter for BamHI (x) PUBLICATION INFORMATION:
        (A) AUTHORS: Gerber, A
                     Krell, S
                     Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997
        (K) RELEVANT RESIDUES IN SEQ ID NO:1: FROM 1 TO 33

(xi) SEQUENCE DESCRIPTION: SEQ ID NO: 5:

TAATAT GGA TCC TGT GCC TCG GGC GCC AAG GAG                                33

(2) INFORMATION FOR SEQ ID NO: 6:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: yes (ix) FEATURE:
        (A) NAME/KEY: 3primer TpN44.5
        (B) LOCATION: TRPTMPA 1230-1210
        (C) IDENTIFICATION METHOD: partial similarity with known
            sequence
        (D) OTHER INFORMATION: 3primer with an adapter for SalI (x) PUBLICATION INFORMATION:
        (A) AUTHORS: Gerber, A
                     Krell, S
                     Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997
        (K) RELEVANT RESIDUES IN SEQ ID NO:1: FROM 1 TO 33

(xi) SEQUENCE DESCRIPTION: SEQ ID NO: 6:

AT GATAGTCGAC TCA TCG AGA GGC TCC TTC TTC                                 33

(2) INFORMATION FOR SEQ ID NO: 7:

(i) SEQUENCE CHARACTERISTICS:
        (A) LENGTH: 33 bases
        (B) TYPE: nucleic acid
        (C) STRANDEDNESS: single
        (D) TOPOLOGY: linear

```
        (ii) MOLECULE TYPE: other nucleic acid
             (A) DESCRIPTION: synthetic oligonucleotide with partial
                 homology to genomic T.

(iii) HYPOTHETICAL: no (iv) ANTI-SENSE: no (ix) FEATURE:
             (A) NAME/KEY: 5primer TpN39(b)
             (B) LOCATION: TRPBMP 348-365
             (C) IDENTIFICATION METHOD: partial similarity with known
                 sequence
             (D) OTHER INFORMATION: 5primer with an adapter for BamHI (x) PUBLICATION INFORMATION:
             (A) AUTHORS: Gerber, A
                          Krell, S
                          Morenz, J
             (B) TITLE: Recombinant Treponema pallidum antigens in
                 syphilis serology
             (C) JOURNAL: Immunobiology
             (D) VOLUME: 196
             (E) ISSUE: 5
             (F) PAGES: 535-549
             (G) DATE: 1996-1997
             (K) RELEVANT RESIDUES IN SEQ ID NO:1: FROM 1 TO 33

(xi) SEQUENCE DESCRIPTION: SEQ ID NO: 7:

TATTAT GGA TCC CAG TCG GCG CTG CAG CCT ATC                             33

(2) INFORMATION FOR SEQ ID NO: 8:

(i) SEQUENCE CHARACTERISTICS:
             (A) LENGTH: 33 bases
             (B) TYPE: nucleic acid
             (C) STRANDEDNESS: single
             (D) TOPOLOGY: linear (ii) MOLECULE TYPE: other nucleic acid
             (A) DESCRIPTION: synthetic oligonucleotide with partial
                 homology to genomic T.

(iii) HYPOTHETICAL: no (iv) ANTI-SENSE: yes (ix) FEATURE:
             (A) NAME/KEY: 3primer TpN39(b)
             (B) LOCATION: TRPBMP 1370-1350
             (C) IDENTIFICATION METHOD: partial similarity with known
                 sequence
             (D) OTHER INFORMATION: 3primer with an adapter for SalI (x) PUBLICATION INFORMATION:
             (A) AUTHORS: Gerber A
                          Krell, S
                          Morenz, J
             (B) TITLE: Recombinant Treponema pallidum antigens in syphilis
                 serology
             (C) JOURNAL: Immunobiology
             (D) VOLUME: 196
             (E) ISSUE: 5
             (F) PAGES: 535-549
             (G) DATE: 1996-1997
             (K) RELEVANT RESIDUES IN SEQ ID NO:1: FROM 1 TO 33

(xi) SEQUENCE DESCRIPTION: SEQ ID NO: 8:

TA TTATGTCGAC TCA CCA GTC GAG CAC CTT GCC                              33

(2) INFORMATION FOR SEQ ID NO: 9:

(i) SEQUENCE CHARACTERISTICS:
             (A) LENGTH: 33 bases
```

```
            (B) TYPE: nucleic acid
            (C) STRANDEDNESS: single
            (D) TOPOLOGY: linear (ii) MOLECULE TYPE: other nucleic acid
            (A) DESCRIPTION: synthetic oligonucleotide with partial
                homology to genomic T.

(iii) HYPOTHETICAL: no (iv) ANTI-SENSE: no (ix) FEATURE:
            (A) NAME/KEY: 5primer TpN47
            (B) LOCATION: TRPANTGEN 100-120
            (C) IDENTIFICATION METHOD: partial similarity with known
                sequence
            (D) OTHER INFORMATION: 5primer with an adapter for  BamHI (x) PUBLICATION INFORMATION:
            (A) AUTHORS: Gerber, A
                        Krell, S
                        Morenz, J
            (B) TITLE: Recombinant Treponema pallidum antigens in
                syphilis serology
            (C) JOURNAL: Immunobiology
            (D) VOLUME: 196
            (E) ISSUE: 5
            (F) PAGES: 535-549
            (G) DATE: 1996-1997
            (K) RELEVANT RESIDUES IN SEQ ID NO:1: FROM 1 TO 33

(xi) SEQUENCE DESCRIPTION: SEQ ID NO: 9:

TAAGAC GGA TCC TGT GGC TCG TCT CAT CAT GAG                                    33

(2) INFORMATION FOR SEQ ID NO: 10:

(i) SEQUENCE CHARACTERISTICS:
            (A) LENGTH: 33 bases
            (B) TYPE: nucleic acid
            (C) STRANDEDNESS: single
            (D) TOPOLOGY: linear (ii) MOLECULE TYPE: other nucleic acid
            (A) DESCRIPTION: synthetic oligonucleotide with partial
                homology to genomic T.

(iii) HYPOTHETICAL: no (iv) ANTI-SENSE: yes (ix) FEATURE:
            (A) NAME/KEY: 3primer TpN47
            (B) LOCATION: TRPANTGEN 1347-1327
            (C) IDENTIFICATION METHOD: partial similarity with known
                sequence
            (D) OTHER INFORMATION: 3primer with an adapter for SalI (x) PUBLICATION INFORMATION:
            (A) AUTHORS: Gerber, A
                         Krell, S
                         Morenz, J
            (B) TITLE: Recombinant Treponema pallidum antigens in syphilis
                serology
            (C) JOURNAL: Immunobiology
            (D) VOLUME: 196
            (E) ISSUE: 5
            (F) PAGES: 535-549
            (G) DATE: 1996-1997
            (K) RELEVANT RESIDUES IN SEQ ID NO:1: FROM 1 TO 33

(xi) SEQUENCE DESCRIPTION: SEQ ID NO: 10:

TA TTAGGTCGAC CTA CTG GGC CAC TAC CTT CGC                                     33

(2) INFORMATION FOR SEQ ID NO: 11:
```

```
    (i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: no (ix) FEATURE:
        (A) NAME/KEY: 5primer TpN29-35
        (B) LOCATION: TRPANT34K 398-421
        (C) IDENTIFICATION METHOD: partial similarity with known
            sequence
        (D) OTHER INFORMATION: 5primer with an adapter for BamHI (x) PUBLICATION INFORMATION:
        (A) AUTHORS: Gerber, A
            Krell, S
            Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997

(xi) SEQUENCE DESCRIPTION: SEQ ID NO: 11:

TTATCT GGA TCC TGC GGG GGC GGT GGA GAG CAT CAG                           36

(2) INFORMATION FOR SEQ ID NO: 12:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: yes (ix) FEATURE:
        (A) NAME/KEY: 3primer TpN29-35
        (B) LOCATION: TRPANT34K 955-932
        (C) IDENTIFICATION METHOD: partial similarity with known
            sequence
        (D) OTHER INFORMATION: 3primer with an adapter for BglII (x) PUBLICATION INFORMATION:
        (A) AUTHORS: Gerber, A
            Krell, S
            Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997

(xi) SEQUENCE DESCRIPTION: SEQ ID NO: 12:

CG GCTAAGATCT CTA CCA CTG AGG CCC CTT CCA TTC                            36
```

-continued

```
(2) INFORMATION FOR SEQ ID NO: 13:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: no (ix) FEATURE:
        (A) NAME/KEY: 5primerwithleader TpN29-35
        (B) LOCATION: TRPANT34K 344-366
        (C) IDENTIFICATION METHOD: partial similarity with known
            sequence
        (D) OTHER INFORMATION: 5primer from signal peptide
            sequence with an adapter for BamHI (x) PUBLICATION INFORMATION:
        (A) AUTHORS: Gerber, A
                 Krell, S
                 Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997

(xi) SEQUENCE DESCRIPTION: SEQ ID NO: 13:

TACAT GGA TCC AAG AGG GTG AGT TTG CTC GGG AG                              34

(2) INFORMATION FOR SEQ ID NO: 14:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: no (ix) FEATURE:
        (A) NAME/KEY: 5primer TpN15
        (B) LOCATION: TPU55214 6859-6879
        (C) IDENTIFICATION METHOD: partial similarity with known
            sequence
        (D) OTHER INFORMATION: 5primer with an adapter for BamHI (x) PUBLICATION INFORMATION:
        (A) AUTHORS: Gerber, A
                 Krell, S
                 Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997

(xi) SEQUENCE DESCRIPTION: SEQ ID NO: 14:

ACCACA GGA TCC TGT TCA TTT AGT TCT ATC CCG                                33
```

(2) INFORMATION FOR SEQ ID NO: 15:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: yes (ix) FEATURE:
        (A) NAME/KEY: 3primer TpN15
        (B) LOCATION: TPU55214 7233-7210
        (C) IDENTIFICATION METHOD: partial similarity with
            known sequence
        (D) OTHER INFORMATION: 3primer with an adapter for SalI (x) PUBLICATION INFORMATION:
        (A) AUTHORS: Gerber, A
            Krell, S
            Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997

(xi) SEQUENCE DESCRIPTION: SEQ ID NO: 15:

```
GA GCGAGTCGAC CTA CCT GCT AAT AAT GGC TTC CTT                              36
```

(2) INFORMATION FOR SEQ ID NO: 16:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: no (ix) FEATURE:
        (A) NAME/KEY: 5primer TpN60
        (B) LOCATION: TPTP4 43-66
        (C) IDENTIFICATION METHOD: partial similarity with known
            sequence
        (D) OTHER INFORMATION: 5primer with an adapter for BamHI (x) PUBLICATION INFORMATION:
        (A) AUTHORS: Gerber, A
            Krell, S
            Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997
        (K) RELEVANT RESIDUES IN SEQ ID NO:1: FROM 1 TO 33

(xi) SEQUENCE DESCRIPTION: SEQ ID NO: 16:

-continued

```
CACAGC GGA TCC GCG AAC GAA TTG CTG TTT AAT                                    33
```

(2) INFORMATION FOR SEQ ID NO: 17:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide with partial
            homology to genomic T.

(iii) HYPOTHETICAL: no (iv) ANTI-SENSE: yes (ix) FEATURE:
        (A) NAME/KEY: 3primer TpN60
        (B) LOCATION: TPTP4 1677-1657
        (C) IDENTIFICATION METHOD: partial similarity with known
            sequence
        (D) OTHER INFORMATION: 3primer with an adapter for SalI (x) PUBLICATION INFORMATION:
        (A) AUTHORS: Gerber, A
            Krell, S
            Morenz, J
        (B) TITLE: Recombinant Treponema pallidum antigens in
            syphilis serology
        (C) JOURNAL: Immunobiology
        (D) VOLUME: 196
        (E) ISSUE: 5
        (F) PAGES: 535-549
        (G) DATE: 1996-1997
        (K) RELEVANT RESIDUES IN SEQ ID NO:1: FROM 1 TO 33

(xi) SEQUENCE DESCRIPTION: SEQ ID NO: 17:

```
GA GAGTGTCGAC TCA ATA CAT ACC TCC CAT ACC                                     33
```